United States Patent
Shimada

(10) Patent No.: US 6,979,312 B2
(45) Date of Patent: Dec. 27, 2005

(54) STEERABLE SHEATH CATHETERS

(75) Inventor: Jin Shimada, St. Paul, MN (US)

(73) Assignee: Biotran Corporation, Inc., St. Paul, MN (US)

(*) Notice: Subject to any disclaimer, the term of this patent is extended or adjusted under 35 U.S.C. 154(b) by 280 days.

(21) Appl. No.: 10/298,864

(22) Filed: Nov. 18, 2002

(65) Prior Publication Data

US 2003/0109861 A1 Jun. 12, 2003

Related U.S. Application Data

(63) Continuation-in-part of application No. 09/833,324, filed on Apr. 12, 2001, now Pat. No. 6,582,536.

(51) Int. Cl.⁷ .............................................. A61M 37/00
(52) U.S. Cl. ...................................... 604/95.01; 604/523
(58) Field of Search .......................... 604/95.01, 524, 604/526, 523, 530, 95.04, 264; 606/192–198; 600/139, 141, 143

(56) References Cited

U.S. PATENT DOCUMENTS

| | | | |
|---|---|---|---|
| 4,430,083 A | 2/1984 | Ganz et al. | 604/283 |
| 4,586,923 A | 5/1986 | Gould et al. | 604/95 |
| 5,527,325 A | 6/1996 | Conley et al. | 606/159 |
| 5,571,086 A | 11/1996 | Kaplan et al. | 604/96 |
| 5,611,777 A | 3/1997 | Bowden et al. | 604/95 |
| 5,702,373 A | 12/1997 | Samson | 604/282 |
| 5,755,704 A | 5/1998 | Lunn | 604/282 |
| 5,769,830 A | 6/1998 | Parker | 604/282 |
| 5,820,592 A * | 10/1998 | Hammerslag | 604/95.01 |
| 5,891,112 A | 4/1999 | Samson | 604/282 |
| 5,916,147 A | 6/1999 | Boury | 600/146 |
| 5,951,495 A | 9/1999 | Berg et al. | 600/585 |
| 5,954,651 A | 9/1999 | Berg et al. | 600/434 |
| 5,961,511 A | 10/1999 | Mortier et al. | 604/527 |
| 5,964,971 A | 10/1999 | Lunn | 156/86 |
| 6,017,335 A | 1/2000 | Burnham | 604/282 |
| 6,027,473 A | 2/2000 | Ponzi | 604/95 |
| 6,030,371 A | 2/2000 | Pursley | 604/282 |
| 6,042,578 A | 3/2000 | Dinh et al. | 604/527 |
| 6,045,734 A | 4/2000 | Luther et al. | 264/103 |
| 6,146,355 A | 11/2000 | Biggs | 604/95.01 |
| 6,171,277 B1 | 1/2001 | Ponzi | 604/95.04 |
| 6,183,435 B1 | 2/2001 | Bumbalough et al. | 604/95.01 |
| 6,251,092 B1 * | 6/2001 | Qin et al. | 604/95.01 |
| 6,716,207 B2 * | 4/2004 | Farnholtz | 604/523 |

FOREIGN PATENT DOCUMENTS

| | | |
|---|---|---|
| EP | 1 075 820 A1 | 8/2000 |
| EP | 1 205 208 A1 | 11/2001 |
| WO | WO 00/67834 | 11/2000 |

* cited by examiner

*Primary Examiner*—Kevin T. Truong
(74) *Attorney, Agent, or Firm*—Kinney & Lange, P.A.

(57) ABSTRACT

The invention is a steerable catheter having a pull wire, a central lumen and a control handle. The central lumen is maintained in a circular shape without obstructions diminishing the useful inter-diameter. The pull wire friction is also reduced by using one wire of larger diameter to create the lumen for the pull wire of smaller diameter, thus reducing the friction on the pull wire and reducing the locking of the catheter body around the pull wire at bends preventing movement of the pull wire. A control handle with a simple operational mechanism that allows direct access to a continuous central lumen from the proximal end of the catheter.

9 Claims, 8 Drawing Sheets

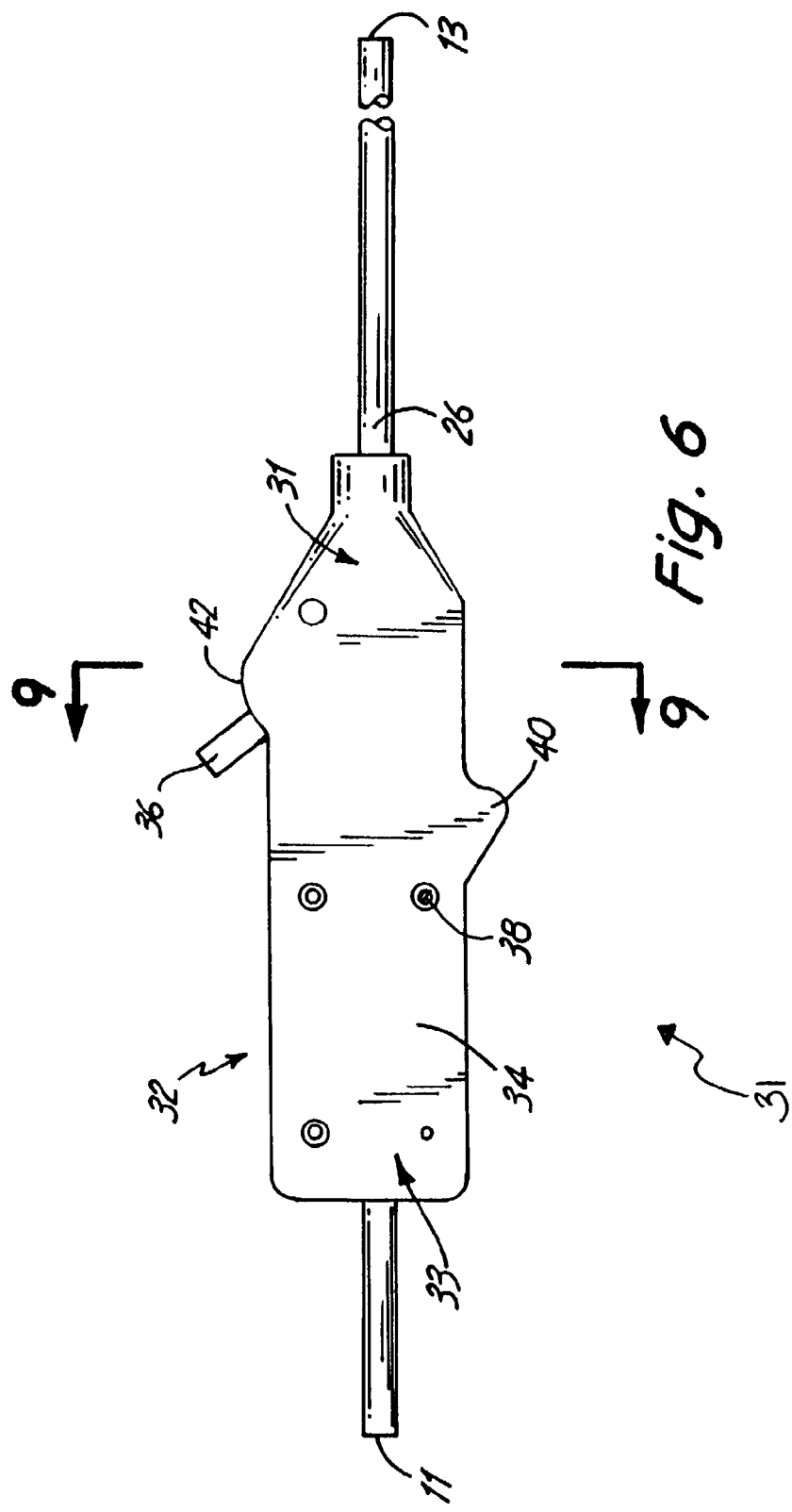

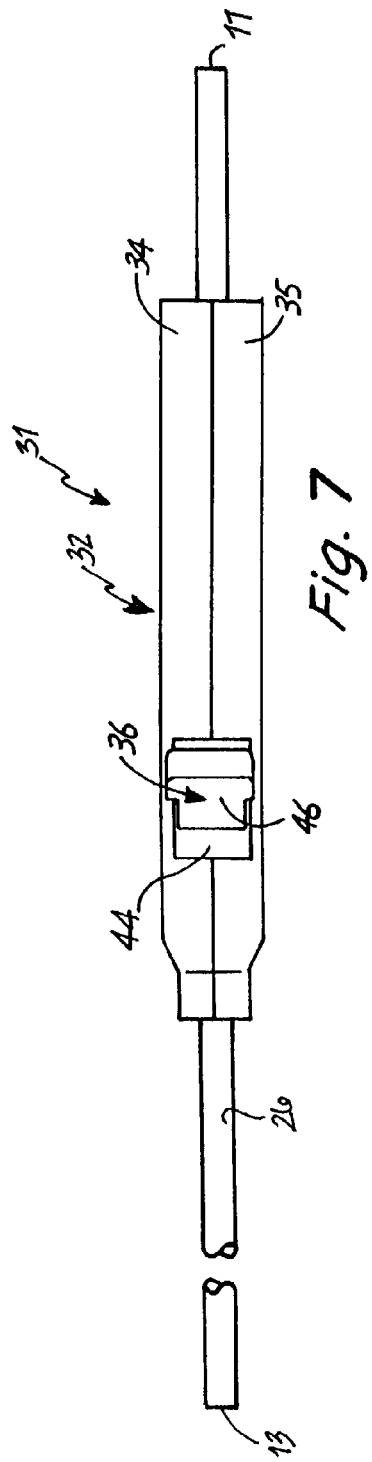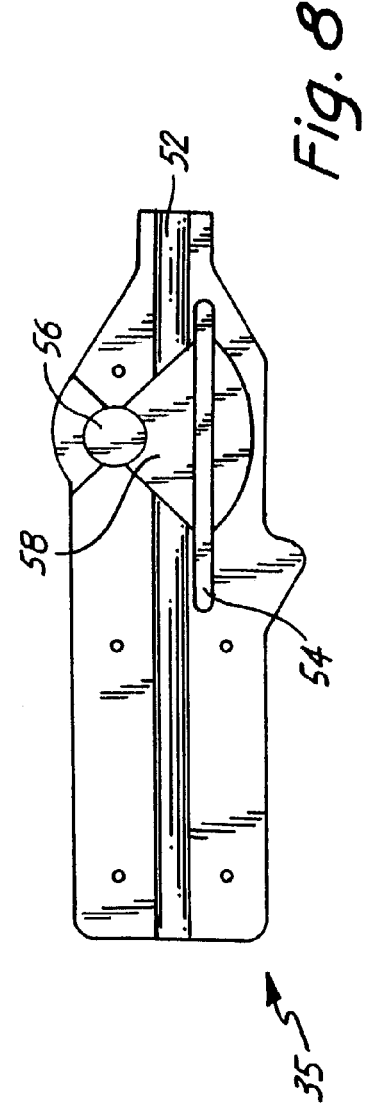

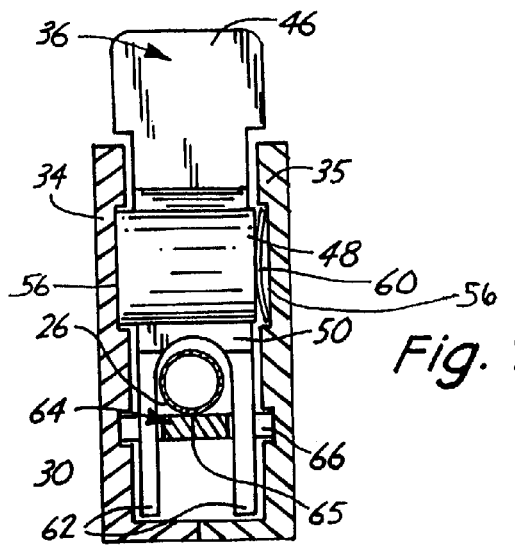
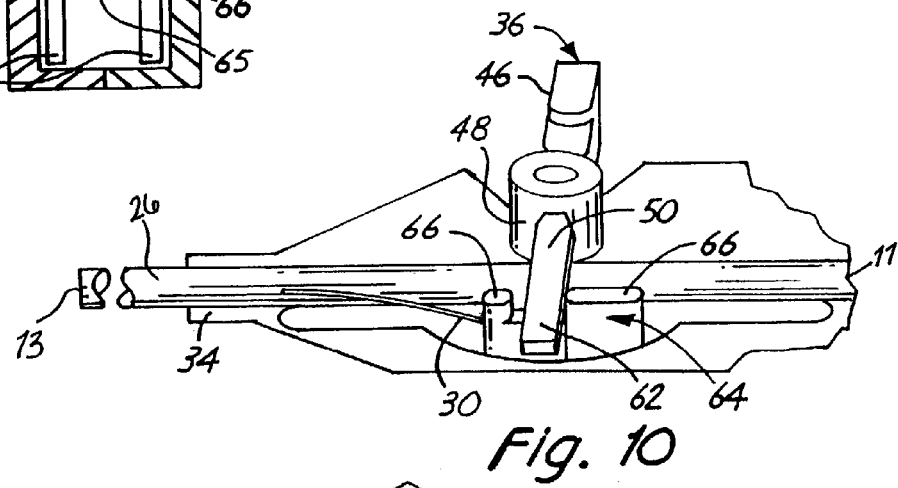
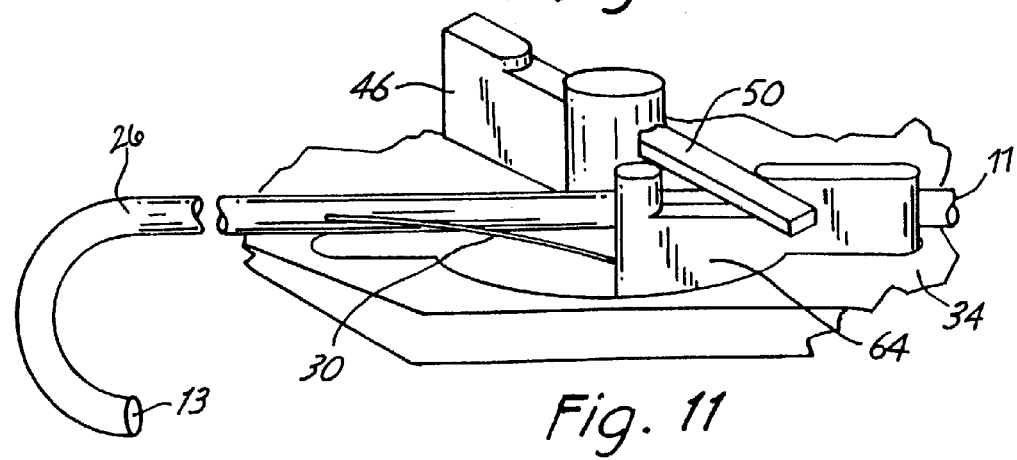

STEERABLE SHEATH CATHETERS

CROSS-REFERENCE TO RELATED APPLICATION(S)

Present application is a continuation in part of application Ser. No. 09/833,324.

BACKGROUND OF THE INVENTION

This invention relates to catheters which are used to provide access into the human body. More particularly, the present invention is directed to steerable sheath catheters which are used to provide access into the human vasculature for delivery of additional tools, instruments, medications or fluids.

Catheters have been commonly used in medical practice to reach locations inside the body otherwise unreachable without surgery. The body of a catheter is long and tubular and contains an inner lumen. A catheter has a distal end or tip which enters the patient as well as a proximal end that has a handle for control by the operator.

The tip of the catheter is first inserted into a major vein, artery or other body cavity. The catheter is then further inserted and guided to the area of concern. The catheter is often used as a delivery method for other tools, such as balloons for performing angioplasty or a camera for performing endoscopy. As medical knowledge increases, the catheterization procedures have become more complicated and more exacting. The usefulness of catheters is largely limited by the ability to successfully manipulate the position and orientation of the catheter tip into small and tortuous vessels. Therefore the goals for a successful catheter design are to maximize the inner diameter while minimizing the outer diameter and maintaining control and flexibility of the catheter body. The catheter operator should be able to easily steer and maintain the catheter shape during use. Additionally, the operator should be able to easily deliver additional tools, instruments, medications or fluids through the inner lumen or lumens by having direct, unhindered access to the inner lumens at the distal end of the catheter.

One method of directing a catheter into position is through the use of a guide wire. First the guide wire is fed into position within the patient. Then the catheter is urged over the guide wire. However, it is not uncommon for the position of the catheter tip to become dislodged from the desired location as the guide wire is removed.

To avoid this problem, other catheters known in the art, are guided into place without the use of guide wires. These catheters have sufficient pushability that the tip of the catheter can be directed from a proximal location without buckling or kinking. Unfortunately, such guide catheters tend to be more difficult to steer into position and the necessary stiffness can limit their placement in areas with sharp curves.

Catheters with tips preformed into particular shapes specialized for specific applications are known in the art. The pre-shaping of the catheter may aid the placement of the tip in the desired location. However, the pre-shaping of catheters for particular applications requires a hospital to provide a wide array of catheter shapes and sizes for use. Another disadvantage to preformed catheters is that they do not allow the physician to adapt the catheter to account for any peculiarities of a patient's vascular system. A physician can attempt to reshape a catheter before use, by applying heat. However, such manual reshaping is not only time consuming but can compromise the lumen of the catheter, by causing the circular lumen to ovalize or flatten out as the catheter is bent, or even kink or seal at a bend destroying the catheter's usefulness.

Steerable sheath catheters, the present invention being one example, are also directed into position from a proximal location. However, the tips of these catheters are steerable due to the action of one or more pull wires that are embedded along the length of the catheter body. Pre-forming of the catheter is not necessary because the operator can adjust the shape of the catheter or steer the tip as the catheter is directed into the body. Therefore these catheters are capable of use in a wider range of procedures than the specialized preformed catheters.

A current method in the art used to manufacture steerable sheath catheters is to form the catheter on a mandrel using multiple layers: an inner liner, a layer of wire braid and an outer thermoplastic jacket. The inner liner is pulled over the mandrel and tightened down. The pull wire is laid axially along the inner liner, often within a groove present on the surface of the mandrel. The steel braid is pulled or woven over the inner liner and pull wire. After the steel braid is tightened down, the entire catheter is encased in a thermoplastic outer jacket. The outer jacket is then encased in heat shrink material and heated. The heat causes the thermoplastic jacket layer to flow, which when teamed with the pressure from the heat shrink material causes the thermoplastic outer jacket to flow into the steel braid consolidating the catheter into one unit. Examples include U.S. Pat. No. 5,669,920; U.S. Pat. No. 6,042,578; U.S. Pat. No. 5,527,325.

The mandrel in this process usually has a longitudinal groove to facilitate the placement of the pull wire during the manufacturing process. The inner liner of the catheter is placed over the mandrel and is pushed into the groove. The pull wire is then laid in the groove on top of the inner liner. The steel braid and outer jacket can then be pulled easily over the mandrel without disturbing the pull wire. However, the use of this process results in the creation of a bulge in the central lumen. This reduces the useable diameter of the central lumen for the insertion of other instruments. In general, it is desirable to maximize the ratio of the inside diameter to the outer diameter of the tubular body of the catheter.

Another problem in the current art is that by embedding the pull wire through the action of a thermoplastic polymer teamed with a heat shrink material or embedding the wire in the catheter body by spraying the outer jacket material over the wire is that the pull wire creates its own lumen, for example as shown in U.S. Pat. No. 6,030,371. Therefore the pull wire and its lumen are approximately equal in diameter. This creates three related difficulties. First, there is friction created between the walls of the lumen and the pull wire as an operator attempts to control the catheter by moving the pull wire. The friction increases the difficulty in operating the pull wire. Second, as the catheter is deflected (bent) through the movement of the pull wire, the steel braid embedded in the outer wall of the catheter is also pulled and flexed. As the steel braid flexes, the forces created can deform the lumen. This can cause the steel braid to lock down on the pull wire and the pull wire lumen. This greatly increases the friction and can prevent movement of the pull wire as the pull wire lumen is deformed from a circular shape into an ovular shape. The third problem is that as the pull wire is "locked down" in the bent catheter, the pull wire and catheter lose the ability to spring back to the original shape as the force on the pull wire from the operator at the proximal end is removed. Accordingly, there remains a need in the art for a catheter with a pull wire with reduced friction and reduced interference from the steel braid which would allow for easier control by the operator and would allow the catheter to return to its original shape.

The pull wire of a steerable catheter is generally manipulated by use of a control handle including a steering mechanism. Control handles and steering mechanisms are available in many different designs according to the number of pull wires, type of catheter steering mechanism used, access ports and desired end use for the catheter. It is preferable that any steering mechanism should be able to be actuated without requiring substantial hand movement and the handle should provide for near simultaneous actuation of both proximal and distal steering. The handle must also be able to meet all appropriate environmental and sterility requirements likely to be encountered. The handle should be able to hold the catheter tip in a bent or deflected condition until the operator actively changes deflection.

In the construction of steerable guide catheters it is additionally beneficial, as previously discussed, to maximize the diameter of the central lumen. Additionally, it is imperative that additional tools and instruments can readily be inserted into the lumen without snagging or jamming in the lumen. In the prior art, the lumens are often not continuous and frequently have a permanent bend as the lumen transitions from the area within the proximal handle portion to the lumen in the catheter body. The discontinuity and indirect route are disadvantages of the current catheter handle and control mechanism designs.

There are two reasons why the catheter body is not continuous until exiting the handle: first, the pull wire must be accessible in order to be attached to the control mechanism within the handle. When the catheter body is manufactured, excess pull wire is left exposed at the proximal end or the body portion is trimmed away to expose sufficient pull wire. However, for convenience of the user the control mechanism usually appears in the middle of the handle where it can easily be manipulated by the user's fingers or thumb, not the end of the handle where the end of the catheter body should be to allow access to the lumen. The prior art solution to the problem of needing access to the pull wire within the handle, is to form a joint in the tubing, including the lumens. The end of the catheter body is placed near the connection point for the steering mechanism. For example, see Gould et al., U.S. Pat. No. 4,586,923. A connecting tube is then glued to the catheter body to extend the lumen towards the exit at the proximal end of the handle, while leaving the pull wire free to attach to the control mechanism within the handle. As it is important for the joint to be strong and not leak, one method of joining is to secure the catheter body inside the connecting tube. This style of attachment causes a size change between the tube end exposed to the user at the proximal end of the handle and the actual size of the lumen inside. This may cause the user to insert the wrong size tool which then jams inside the handle. The user may waste several sterile tools before the one that fits is found. As all these products are sterile and cannot be reused, the search for the correct fit is a waste that could be avoided.

Additionally, the joint, of either an overlapping type described above, or a butted joint, may impede the insertion of instruments. In the overlapped joint, the instruments are likely to hit or be snagged upon the catheter body inside of the connecting tube at the position of the joint. At best, the operator will have to redirect the inserted instrument passed the blockage into the inner lumen, and at worse may damage the instrument being inserted. In a butted joint where the two tubes are glued end-to-end, there is a potential problem if the joint is not made exactly, or if glue leaks inside of the joint that may cause blockage similar to that with the overlapping joint. Also, if the lumen is to be used for the delivery of fluids or medication, there is the potential at any joint for leakage, which may be detrimental by contaminating any samples that are being taken, delivering an imprecise amount of medication, and fluid escaping the lumen and entering the handle body and leaking out into the sterile surgical environment.

The second problem preventing the use of a continuous, direct catheter body is the type of control mechanism used. Often the bulk or design of the control mechanism limits the size of the lumen, or lumens as shown in U.S. Pat. No. 5,571,086. The design may also force the redirection of the lumen, or lumens to avoid parts of the control mechanism. Both are disadvantages when use of the lumen is desired for the insertion of tools.

There is a need in the art for a simple steering mechanism. One that is simple to use, easy to construct and low in cost. There is also need for a steering mechanism that does not impede the central lumen by requiring additional joints, bends, or variation in size of the lumen.

It is preferable that any steering mechanism should operate without requiring substantial hand movement and the handle should provide for near simultaneous actuation of both proximal and distal steering. The handle must also be able to meet all appropriate environmental and sterility requirements likely to be encountered. The handle should be able to hold the tip assembly in a bent or deflected condition until the operator actively changes deflection.

BRIEF SUMMARY OF THE INVENTION

The invention includes a steerable sheath catheter and control handle design utilizing a pull wire control mechanism. A central lumen passes directly through the catheter without size changes, bends or joints that would impair the utility of the lumen. The pull wire friction is also reduced by the improved control mechanism by allowing straight line operation of the pull wire without the necessity of a separate locking mechanism. The control handle and steering mechanism additionally allow direct access to the continuous central lumen.

BRIEF DESCRIPTION OF THE DRAWINGS

FIG. 6 is a side view of the catheter.
FIG. 7 is a top view of the proximal end of a catheter including the first handle embodiment.
FIG. 8 is a perspective view of the inner surface of the left handle body.
FIG. 9 is a cross-sectional view taken along the Line 9—9 in FIG. 6.
FIG. 10 is a perspective view of the catheter in the initial position with the left handle body section removed.
FIG. 11 is a perspective view of the catheter in the curved position with the left handle body removed.

DETAILED DESCRIPTION

Figure 1:
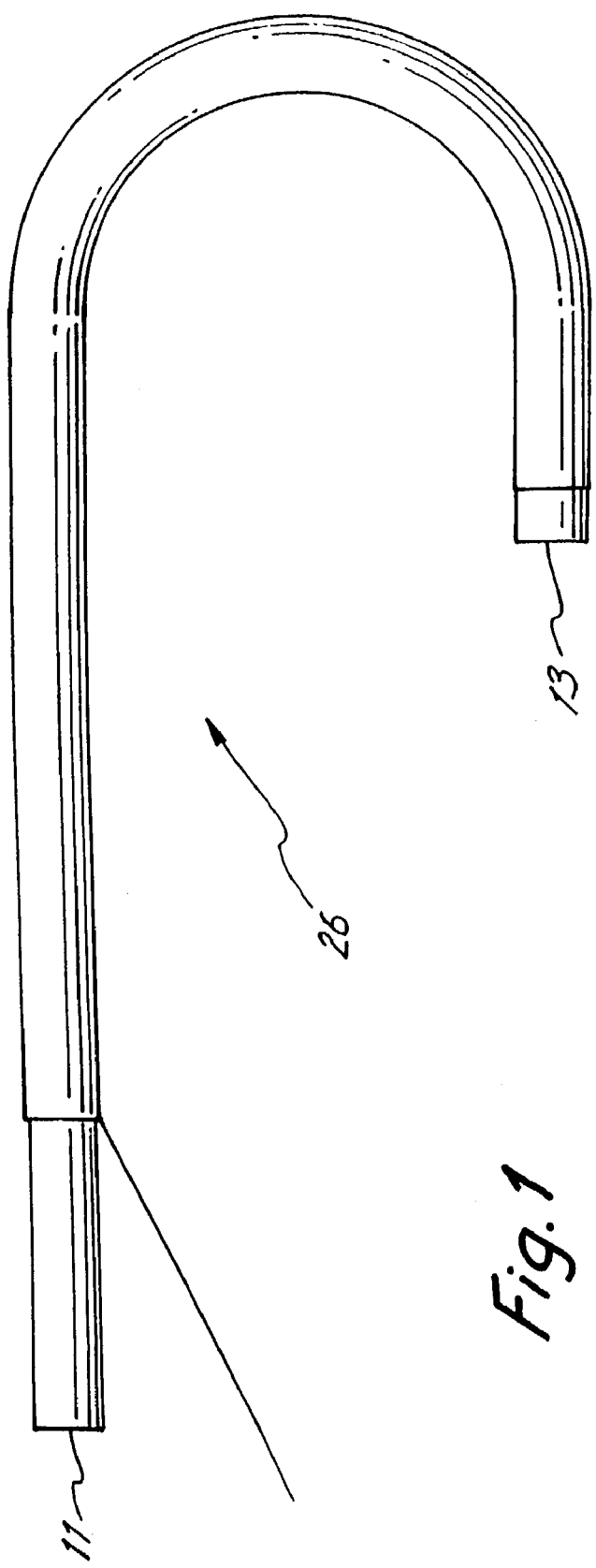
FIG. 1 is a perspective view of the catheter.

The present invention provides an improved catheter that maximizes the usable inner diameter, minimizes pull wire friction and allows easy access to the inner lumen or lumens. The inventive control handle design provides for an improved catheter that allows direct and unhindered access into the central lumen while still allowing easy pull wire control of catheter deflection without requiring the controller to maintain the position of the control mechanism manually or the use of additional locking mechanisms. The novel control handle design is also adaptable to virtually any catheter body design. The lack of necessity for an additional locking mechanism, ease of operation and reduced cost are additional benefits of the new design.

The usable inner diameter of the catheter body is maximized compared to the outer diameter by modifying manufacturing techniques. The pull wire is not laid into a groove in the mandrel. Therefore, there is no predisposition to form a bulge within the inner lumen of the catheter. Also, the shape of the outer jacket material has been modified from a tube with circular cross-section and uniform thickness to a tube with elliptical or ovular cross-section and uneven thickness. The outer jacket material is thicker at the position of the pull wire. When the outer jacket material is heated until it flows, the material will redistribute around the circumference of the catheter body due to the force of the heat shrink material. The result is an approximately circular catheter with the pull wire embedded within the outer jacket, not protruding into the inner lumen nor bulging out of the outer diameter.

The outer diameter of the catheter is minimized at the tip by a novel treatment method used on the wire braid. The wire braid is formed on a disposable core. An end section of the wire braid is heat tempered and cooled before incorporation into the catheter body. The action of heat tempering the section of wire braid placed at the tip of the catheter releases the stress on the wire and reduces radial forces. Without heat tempering, the wires maintain the stress from being braided, the braid patterns provide radial pressure or outward force at the ends of the braid resulting in a distorted braid pattern. The invention prevents the problem encountered in the prior art of the ends of the wire braid flaring and protruding through the outer jacket of the catheter. In the prior art, the wire braid is contained either through the application of additional material or changing the manufacturing process of the catheter so that the outer jacket material is not heated until fluid. There are problems with both techniques. When additional material is added at the tip of the catheter, an undesirable bulge is formed in that area. If the manufacturing process is changed to deter wire protrusion by incompletely melting the outer jacket material, often the result is incomplete integration and lamination of the catheter, which can result in failure of the catheter.

One alternative method in the prior art would be to heat treat the entire wire braid. However, there is a loss of radial force capacity and the possibility of increased kinking of the wire braid when the entire length of it is heat tempered. Also, the wire will not expand as desired to into the outer jacket material when the outer jacket material is liquified. The result is a less flexible catheter with possible increased interference between the pull wire and wire braid as well as problems with integrity of the lamination process.

Another method in the prior art to prevent the wire braid from flaring out of the catheter body, is to place an additional piece of polyester around the end of the wire braid. The polyester has a higher melting point than the outer jacket material. Therefore, when the outer jacket material is liquified to allow it to flow into the wire braid, the wire braid remains contained and does not escape from the catheter. The problem with the addition of this additional polyester material is that an undesirable bulge is created on the distal end of the catheter where this additional material is added. An additional problem of poor bonding due to differences in the materials and their melting points can also occur.

To minimize pull wire friction, the present invention uses one wire to create a lumen and then removes that wire and replaces it with a smaller diameter pull wire in order to control the catheter. The benefit of having a pull wire with a smaller diameter than the lumen is to allow easier movement of that pull wire through the reduced friction of contact between the lumen and the pull wire. An additional benefit is that as the catheter is bent, there is additional space inside the lumen, so as the wire braid is pulled, thereby placing force onto the lumen, the pull wire will not become as easily locked down by the changed shape of the lumen. If the pull wire is the same size as the lumen as it is in prior art applications, the wire braid can lock down the pull wire and prevent its movement as the lumen is deformed from a circular shape into an ovular shape. This problem may require a catheter to have multiple pull wires just to allow the catheter to move in one plane. If a pull wire in the current art becomes locked down as the catheter is bent, operation of a pull wire on the opposite side is necessary to return the catheter to its original straight configuration. In the current invention, because the lumen is larger than the pull wire, forces placed on the lumen by the wire braid are much less likely to lock down the pull wire and preventing its free movement and control of the catheter. Therefore, the inventive catheter can return to its original straight configuration simply by releasing the force on the pull wire. In summary, the inventive catheter allows a pull wire with free movement without any loss in internal or external space and also has increased flexibility because the braid will not lock up the pull wire.

The novel control handle design allows for easy one hand operation of the catheter steering mechanism. The steering mechanism does not require a locking mechanism because the position steering mechanism and the operationally attached pull wire are controlled by frictional means. Consequently, the controller of the catheter does not have to maintain the position of the control mechanism manually during use, once the catheter is properly positioned. The pull wire moves only when actuated in either the distal or proximal direction by operator movement of the steering mechanism.

The steering mechanism is also designed in such a way that allows the body of the catheter, including a central or multiple lumen(s), to pass directly through the handle without interference by the steering mechanism. The central lumen preferably has the same diameter within the handle as in the body of the catheter to provide a continuous and unhindered passage. By allowing the catheter body, and the central lumen inside, to pass unhindered directly and continuously through the handle and steering mechanism to an external port proximal to the controller, the inventive mechanism allows for easy insertion of additional instruments or tools by the operator without risks that the tool will be mismatched in size or will jam on an internal size change, joint seam, or bend in the lumen.

The inventive mechanism reduces the force needed to actuate the pull wire by allowing the pull wire to move parallel to the catheter body in a straight line without requiring the pull wire to be deflected at a sharp angle to reach the steering mechanism. Movement of the pull wire in a direction approximately in line with the path of the pull wire through the pull wire lumen also reduces the friction of the catheter body on the pull wire. The pull wire is directly affected by the manipulation of the control mechanism of the operator and is therefore sensitive enough to allow tight control of the catheter tip movements.

The handle design complements the improved method for making the handle body, also disclosed herein, by maintaining the reduction in pull wire friction and allowing the maximized central lumen diameter in ratio to the outer diameter to not be compromised by the steering mechanism.

The basic structure of a catheter body generally indicated at 26 made in accordance with the present invention is illustrated in FIG. 1. The catheter body 26 extends from a proximal end 11 to a distal end 13. The proximal end 11 will generally be attached to a handle (not shown), while the distal end 13 contains the catheter tip which is inserted into the body. The overall length of the catheter may be varied as necessary for various applications. Typical catheter lengths will be on the order of 20–60 inches, with a preferred length of 48 inches.

Figure 2:
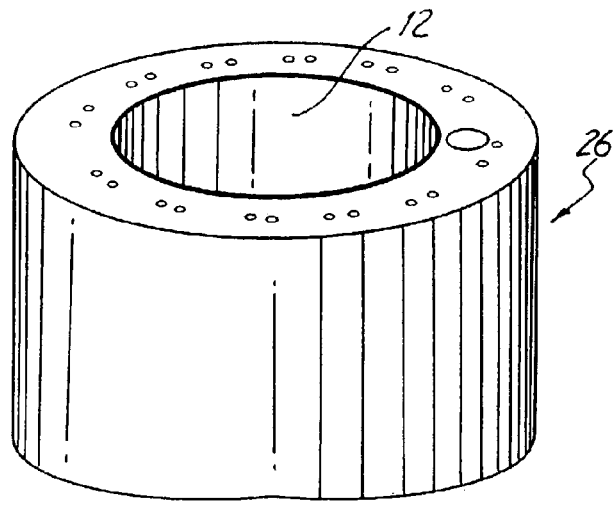
FIG. 2 is a perspective view of the catheter body.

The catheter body 26 is generally tubular in shape and desirably includes a central lumen 12 as illustrated in FIG. 2. Alternative embodiments include more than one lumen or subdividing a large lumen into two or more separate lumens, such as in balloon angioplasty.

Figure 3:
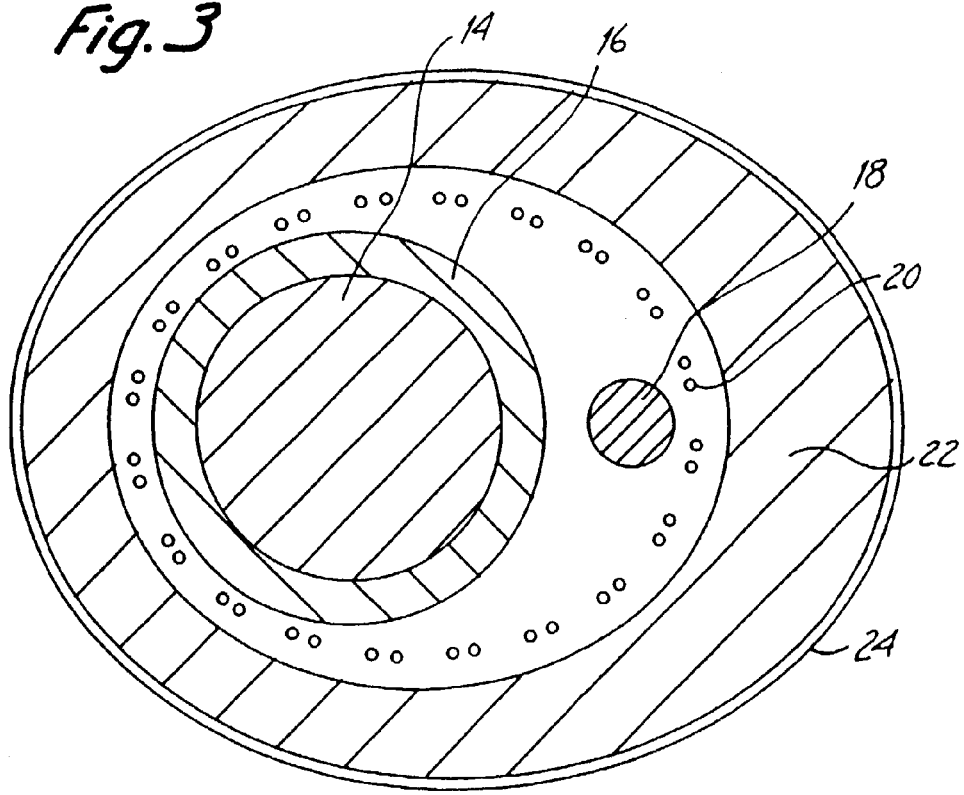
FIG. 3 is a cross-sectional view of the catheter body before lamination by heating.

The basic method of manufacture according to a first embodiment of the present invention will be described below and illustrated in FIG. 3. The catheter components as they are assembled and after completion will be collectively referred to as a catheter body 26. A ground mandrel 14, which is preferably approximately 4 feet in length, is the first component of the catheter body 26. The mandrel 14 has two ends named for reference the distal and the proximal ends. The inner liner 16 is placed on the mandrel 14. The inner liner 16 is preferably an extruded Teflon® (polytetrafluoroethylene) tubing, which is available commercially. The inner liner 16 is knotted at one end (e.g. the distal end) and is fed on to the mandrel 14. It is snugged down by pulling and knotted on the other end (e.g. the proximal end) also.

A lumen defining wire 18, is placed longitudinally along the inner liner 16. The lumen defining wire 18, is composed of stainless steel and is preferably approximately 0.010 inches in diameter. In alternate embodiments the lumen defining wire 18 may be encased inside another Teflon® tube or coated with lubricant before placement.

A wire braid 20, which is either purchased separately or braided on site, is formed onto disposable core material in order to achieve the proper diameter. The wire braid 20 is preferably composed of φ0.003 high tensile stainless steel wire. The wire braid 20 is formed in a standard braid pattern with preferably approximately 16 wires at 45–60 PPI. Before the wire braid 20 is placed onto the catheter body 26, one end is heat tempered with a torch or alternate heat source. The wire braid 20 is cooled, removed from the disposable core material and carefully slid over the catheter body 26. It is necessary that care is taken not to disturb the position of the lumen defining wire 18, which must remain straight. The end of the wire braid which has been heat treated or annealed terminates somewhat before the distal end 13 of the mandrel 14. The untreated end of the wire braid 20 is knotted at the proximal end 11 of the mandrel 14. Therefore, at the distal end 13 of the assembly both the inner liner 16 and the lumen defining wire 18 are exposed.

An outer jacket 22 is slid over the catheter body 26. The outer jacket 22 is a tube extruded from Pebax® before application to the catheter body 26. Pebax® is a thermoplastic elastomer resin by the Atochem Corporation of France. The outer jacket 22 is made of either single or multiple sections of tubing that are butted together over the catheter body 26 leaving the distal end of the wire braid 20 exposed. Different sections of the outer jacket 22 may have different softness/stiffness (tensile) characteristics in order to facilitate particular features in the catheter body. For example, a bending region may have an outer jacket section that has greater softness than a region that will remain straight.

A tube of heat shrink material 24 is placed over the top of the outer jacket 22. The heat shrink material 24 is a fluoropolymer or polyolefin material. FIG. 3 displays a cross-section of the catheter body 26 before lamination of the materials by heating.

Next, the entire catheter body 26 is laminated by heating until the outer jacket 22 liquefies. The heat shrink material 24 has a higher melt temperature than the outer jacket 22 and when it constricts, the heat shrink material retains its tubular shape thereby forcing the liquefied outer jacket 22 into the wire braid and into contact with the lumen defining wire 18 and inner liner 16. The catheter body 26 is cooled and the outer jacket 22 solidifies. The heat shrink material 24 is scored and cracked open in order to remove it. After removal, the outer jacket 22 becomes the outside layer of the catheter body.

Figure 4:
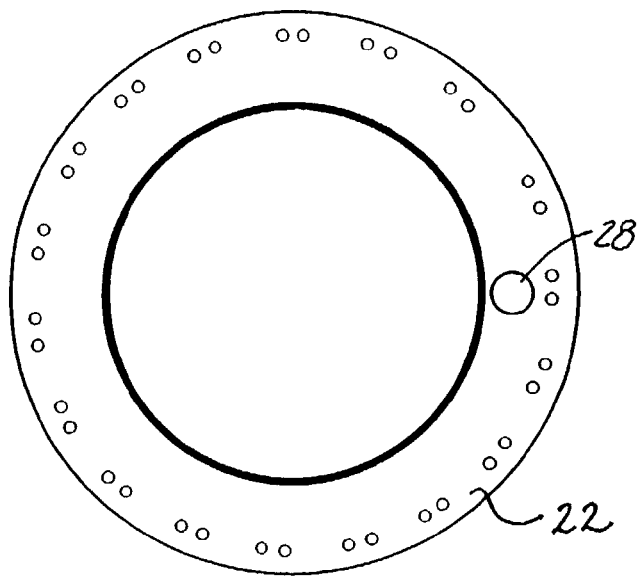
FIG. 4 is a cross-sectional view of the catheter body after lumen-defining wire is removed.
Figure 5:
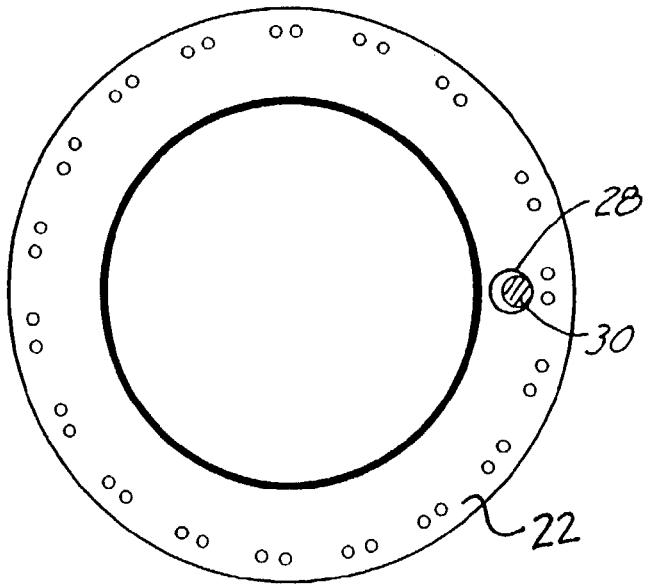
FIG. 5 is a cross-sectional view of the catheter body after insertion of pull wire into the lumen.

Next the lumen defining wire 18 is removed from the distal end and removed from the catheter body 26. A lumen 28 for placement of a pull wire 30 remains in the outer jacket 22 as displayed in FIG. 4. A permanent pull wire 30 is inserted into this lumen 28 from the distal end of the catheter body 26 as displayed in FIG. 5. At the end of the pull wire 30 is attached to a pull ring which is placed around the distal end of the catheter body 26. The permanent pull wire 30 has a diameter of preferably approximately 0.008 inches. The diameter of the permanent pull wire 30 is smaller than the lumen defining wire 18. Alternate embodiments include coating the permanent pull wire 30 with Teflon®, marketed by E.I. duPont de Nemours and Company Corporation of Wilmington, Del., or lubricants, such as silicones so that the wire is more easily moved within the lumen.

After the permanent pull wire 30 and attached pull ring are in place, another section of outer jacket made from Pebax® is placed on the distal end of the catheter body 26, over the exposed mandrel, permanent pull wire 30, pull ring and annealed wire braid. This distal end section of Pebax® material is also covered with heat shrink tubing and is heated until the Pebax® material is liquified. When liquified, this distal end section flows to connect with the main section of outer jacket and captures the pull ring of the permanent guide wire. The pull ring is fully secured to the catheter body by the Pebax® polymer when the heating and cooling of the catheter body is complete and the heat shrink tubing is once again removed. The mandrel is removed from the completed catheter body 26 which is ready for installation of a handle on the proximal end 11.

An exemplary handle consistent with the first embodiment is generally indicated in FIG. 6. The inventive handle allows the catheter body 26 to pass through the handle 32 without obstruction while allowing easy control of the pull wire 30 (not shown). The first handle embodiment 31 comprises a handle 32 a control lever 36, which separates vertically into left and right portions. The right portion 34 is shown in FIG. 6. The right and left portions, 34, 35 (not visible) sandwich the catheter body 26 between them and are secured together with screws 38 or other suitable fastening means. The handle 32 also may have a shaped grip portion 40 and/or top portion 42 to allow for easier gripping of the handle by the operator.

The top portion 42 has a opening 44 as illustrated in FIG. 7. Control lever 36 is positioned through opening 44 such that an upper paddle portion 46 is projected above the top portion 42 and connects with additional portions of the control lever 36 inside the handle 32.

The right and left portions 34, 35 of the handle 32 are approximately mirror images of each other except for alterations to accommodate fasteners, for example, the screw head recesses in one portion. Suitable materials for the handle components include, but are not limited to: polyacetal, Lexan® made by GE Plastics, Rilsan® made by Atochem Corporation, EVA, polypropylene, LDPE, HDPE, and other thermoplastics. The internal structure of the left portion 35 is illustrated in FIG. 8. The right and left portions 34, 35 each comprise a channel 52, a track 54, a socket 56 and a sweep zone 58. Channel 52 holds catheter body 26, which maybe secured into either the right or left portion 34, 35 by adhesive means.

As illustrated in FIG. 9, the control lever 36 has an upper paddle portion 46, a pin 48, and a lower fork portion 50. The ends of pin 48 mate with the sockets 56 of the right and left portions 34, 35 of the handle. A curved washer 60 is biased between one end of pin 48 and socket 56 of the left portion 35 of the handle. The pin is operably connected within socket 56 with the curved washer 60 so as to allow rotational movement of the pin, but not lateral movement of control lever 36. The curved washer 60 may be placed on either end of pin 48 relative to the right or left side of the handle. Preferably, a curved washer 60 may be placed on both ends of pin 48 adjacent to the right and left portions 34, 35.

The lower fork portion 50 of control lever 36 is divided into two legs 62 which intermesh with slide 64. Slide 64 has an "H"-like shape, wherein the four side ends 66 of the slide 64 ride in track 54 of the right and left portions 34, 35. Suitable materials for slide 64 include, for example, aluminum and stainless steel. The legs 62 project between the side ends 66 of slide 64. The pull wire 30 exits the catheter body close to slide 64 and is fastened to slide 64 through a central bore 65. Exemplary fastening means include a set screw and adhesives.

The pull wire 30 may be exposed from the continuous catheter body by the following means: a small slit is cut in the outer jacket of the completed catheter body at the location where the pull wire 30 should exit for attachment to the slide. A tool is then used to draw the end of the pull wire 30 out through the slit in the outer jacket allowing for attachment to the slide. The novel method of manufacturing the catheter body of this invention, allows for the pull wire 30 to be visible underneath the outer jacket layer and therefore can readily be accessed by this method.

The control lever 36 is in the initial position as illustrated in FIG. 10. In the initial position, tension has not been applied to the pull wire 30 therefore, the catheter tip is in a linear conformation. The curved washer 60 biased between pin 48 and socket 56 prevents movement of the control lever 36 when force has not been applied to the control lever 36.

In order to cause deflection of the distal end 13 of the catheter body 26, the upper paddle portion 46 of the control lever 36 is pushed towards the distal end 43 of the catheter. The movement of the upper paddle portion 46 causes rotation about an axis through pin 48 causing the lower fork portion 50 to swing in the direction opposite to the upper paddle portion. Movement of the lower fork portion 50 towards the proximal end 11 of the catheter handle likewise causes the interlocked slide to also move towards the proximal end 11 of the catheter in tracks 54. The proximal movement of the slide 64 pulls the pull wire 30, which causes curvature of the distal end 13 of the catheter body 26 as illustrated in FIG. 11.

The process maybe reversed. If the upper paddle portion 46 of FIG. 11 is pulled toward the proximal end 11 of the handle, the slide will be pushed toward the distal end 13 of the handle, thereby pushing the pull wire 30 into the catheter body 26 causing the distal end 13 of the catheter body 26 to straighten.

Figure 12:
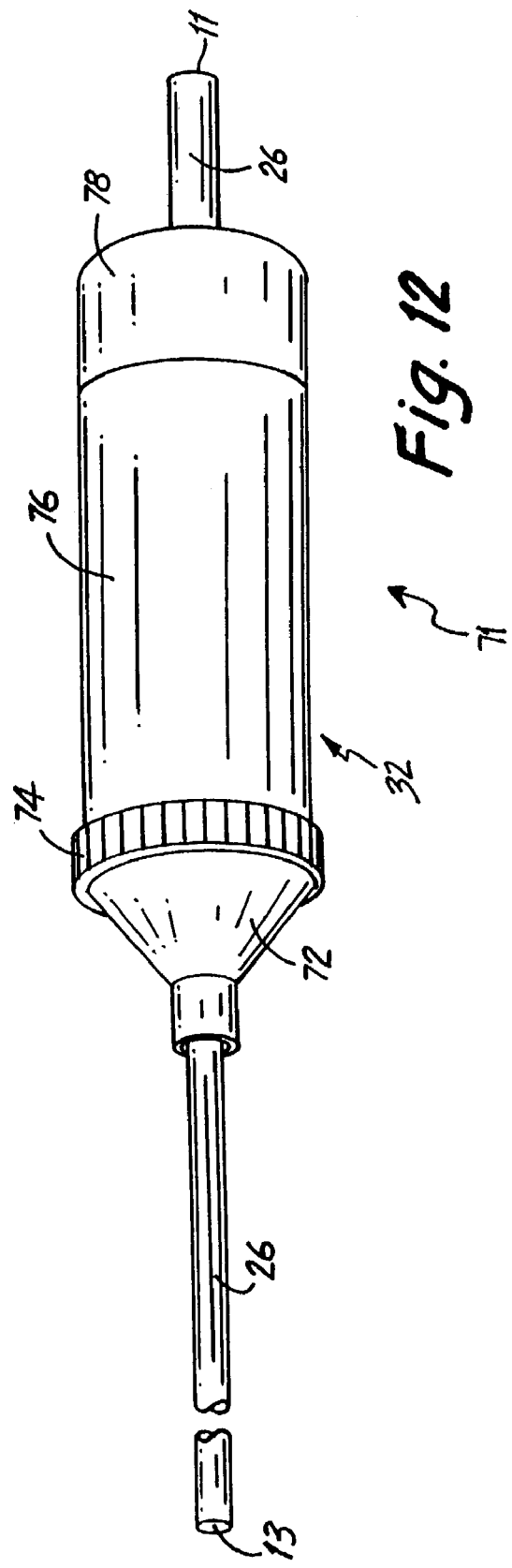
FIG. 12 is a perspective view of a catheter including the second handle embodiment.

A second handle embodiment generally indicated at 71 in FIG. 12, also allows the catheter body 26 to pass through the handle 32 without obstruction while allowing easy control of the pull wire 30 (not visible). The second handle embodiment 71 moves the pull wire parallel to the catheter body 26 in approximately a straight line. The second handle embodiment 71 is comprised of nose 72, wheel 82, which is a portion of displacement member 74, grip 76, and cap 78, which make up handle 32 surrounding catheter body 26 adjacent to proximal end 11. The catheter is controlled by holding the handle 32 at grip 76 and rotating wheel 82 either clockwise or counterclockwise thereby bending or straightening the catheter body 26 through action of defection mechanism 92 on the pull wire 30 inside the handle 32.

Figure 13:
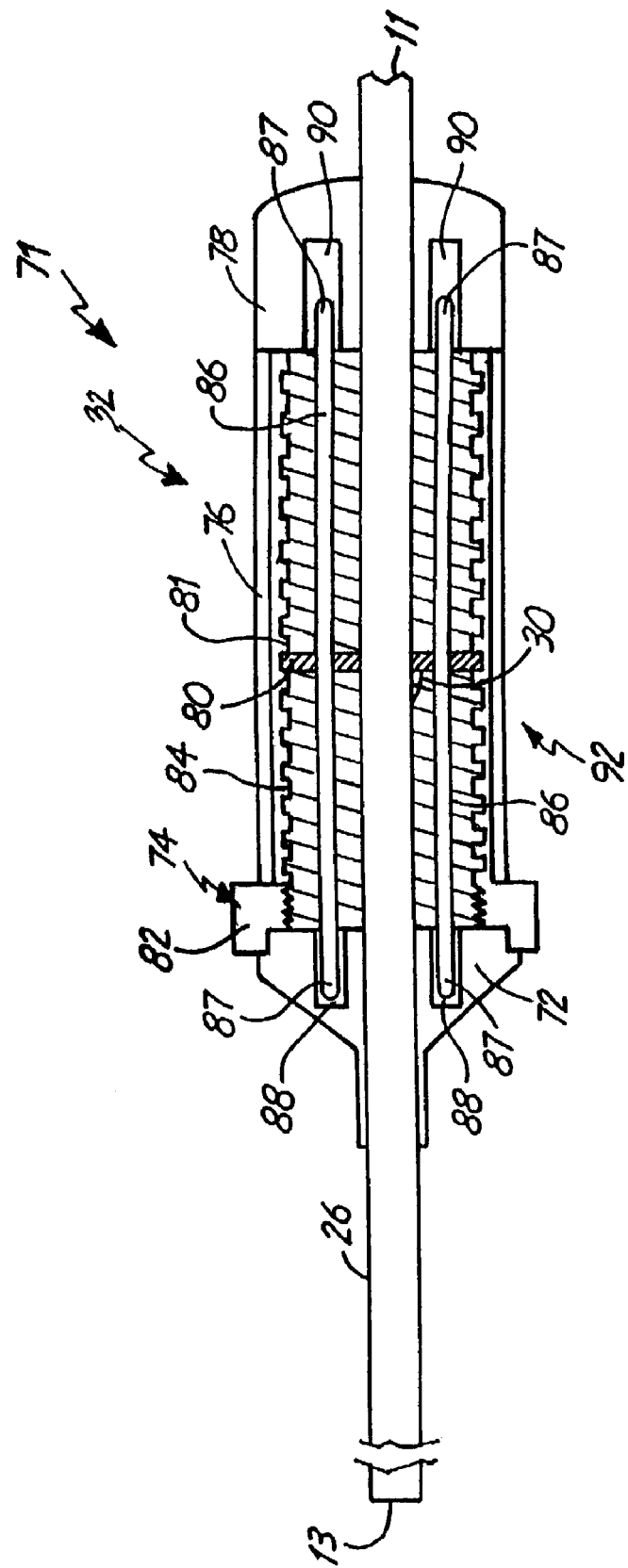
FIG. 13. is a cross-sectional view through the second handle embodiment.

The deflection mechanism 92 comprises nose channels 88, struts 86, cap channels 90, shuttle 80 having edge 81, displacement member 74 including wheel 82 and groove 84, which are illustrated in FIG. 13. Nose 72 and cap 78 each carry two channels, nose channels 88 and cap channels 90 respectively. The channels 88, 90 carry struts 86, such that one end 87 of the strut is within a nose channel 88 and one end 87 of the strut is within a cap channel 90. Additionally, the channels are of sufficient length to allow longitudinal movement of strut 86 without ends 87 leaving the channels 88 or 90. The struts 86 are placed parallel to catheter body 26, which passes approximately centrally through handle 32. The struts 86 are attached to shuttle 80. Catheter body 26 is not attached to shuttle 80, but passes continuously through shuttle 80 without impairing movement of shuttle 80 parallel to the catheter body 26.

The edge 81 of shuttle 80 is operably connected to groove 84 of displacement member 74. Edge 81 travels within groove 84 such that rotation of wheel 82 causes groove 84 to travel around edge 81 of shuttle 80 thereby displacing shuttle 80 and struts 86 relative to catheter body 26. Pull wire 30 exits catheter body 26 and is attached to shuttle 80. Alternatively, pull wire 30 could be attached to struts 86. When the displacement member 74 is rotated by a wheel 82, grooves 84 are rotated relative to shuttle 80 causing linear displacement of shuttle 80 with attached pull wire 30 parallel to catheter body 26 either towards the distal tip 13 or proximal end 11 according to rotation direction of wheel 82 and orientation of groups 84.

To steer a catheter with the second handle embodiment, an operator holds the handle 32 at grip 76 and rotates wheel 82 counter-clockwise, for example. The counterclockwise movement of wheel 82, rotates displacement member 74 including groove 84. The groove 84 travels around edge 81 of shuttle 80, thereby displacing shuttle 80 towards the proximal end 11. The displacement of shuttle 80, likewise displaces the attached pull wire 30 towards the proximal end 11 causing the distal end 13 of the catheter body 26 to curve (not shown). Subsequent rotation of displacement member 74 in the clockwise direction, thereby straightens the catheter body 26 by displacing shuttle 80 towards the distal end 13, thereby pushing the pull wire 30 into the pull wire lumen of catheter body 26. The relationship of clockwise and counterclockwise motion to the displacement of shuttle 80 is readily modified by changing the direction and pitch of groove 84 within displacement member 74. When no rotational force is applied to wheel 82, frictional forces between groove 84 and shuttle 80, in addition to other contacting portions of deflection mechanism 92, prevent the pull wire from moving. Struts 86 prevent the rotation of shuttle 80 relative to the catheter body 26.

Both the first handle embodiment 31 and second handle embodiment 71 provide for displacement of the pull wire 30 parallel to the catheter body 26 without altering the approximately straight line path of the pull wire 30 within the handle 32. Additionally, the catheter body 26 passes through handle 32 without internal size change, joint, seam, bend or other feature changes that would impair the usefulness of the inner lumen or lumens. The inventive control handle embodiments provide for an improved catheter that allows direct and unhindered access into the central lumen while still allowing easy pull wire control of catheter deflection without requiring the controller to maintain the position of the control mechanism manually or requiring additional locking mechanisms.

Although the present invention has been described with reference to preferred embodiments, workers skilled in the art will recognize that changes may be made in form and detail without departing from the spirit and scope of the invention.

What is claimed is:

1. A steerable sheath catheter having a proximal end and a distal end, wherein the catheter comprises an inner liner defining a central lumen, a pull wire, a wire braid surrounding the inner liner, an outer jacket surrounding the wire braid, and a control handle, the improvement comprising:
    a mechanism that displaces the pull wire longitudinally relative to the catheter, wherein the mechanism is operably connected to the control handle and further comprises:
        a slide attached to the pull wire; and
        a control lever having a lower portion, an upper portion, and a pin between the upper portion and the lower portion, wherein the lower portion is operably intermeshed with the slide, and wherein the pin is pivotally connected to a socket, whereby actuation of the upper portion causes deflection of the pull wire;
    extending the pull wire from the distal end to an opening in the outer jacket between the distal end and the proximal end, wherein the pull wire exits the outer jacket at the opening and is operably connected to the mechanism that displaces the pullwire; and
    wherein the central lumen extends continuously and linearly through the mechanism that displaces the pullwire.

2. The steerable sheath catheter of claim 1 wherein the control handle surrounds a portion of the outer jacket, the portion containing the opening for the pull wire.

3. The steerable sheath catheter of claim 1 wherein the central lumen has an inner diameter and the outer jacket has an outer diameter such that the ratio of the inner diameter to the outer diameter is maximized.

4. The steerable sheath catheter of claim 1 wherein the wire braid has an end portion and the end portion is heat treated.

5. A steerable catheter comprising:
    a continuous catheter body having at least one continuous inner lumen, a pull wire, a pull wire lumen, a proximal end and a distal end;
    a control handle having a proximal end and a distal end, the control handle mounted on the continuous catheter body such that the proximal end of the continuous catheter body extends beyond the proximal end of the control handle; and
    a mechanism that displaces the pull wire, wherein the mechanism is operably connected to the control handle, the mechanism comprising:
        a slide attached to the pull wire; and
        a control lever having a lower portion, an upper portion, and a pin between the upper portion and the lower portion, wherein the lower portion is operably intermeshed with the slide, and wherein the pin is pivotally connected to a socket, whereby actuation of the upper portion causes deflection of the pull wire.

6. The steerable catheter of claim 5 wherein the inner lumen has substantially the same diameter from the proximal end of the catheter body to the distal end of the catheter body.

7. A steerable catheter comprising:
    a catheter body extending from a distal end to a proximal end, the catheter body comprising:
    at least one continuous inner lumen;
    a pull wire;
    a pull wire lumen having a diameter relatively larger than the pull wire diameter such that the pull wire operably displaces within the pull wire lumen;
    a wire braid surrounding the lumen, pull wire lumen and pull wire;
    an outer jacket surrounding the wire braid; and
    a control handle attached to the catheter body between the distal end and the proximal end, the control handle including a mechanism that linearly displaces the pull wire, the mechanism comprising:
        a slide attached to the pull wire; and
        a control lever having a lower portion, an upper portion, and a pin between the upper portion and the lower portion, wherein the lower portion is operably intermeshed with the slide, and wherein the pin is pivotally connected to a socket, whereby actuation of the upper portion causes deflection of the pull wire.

8. The steerable catheter of claim 7 wherein the wire braid has an end portion and the end portion is heat treated.

9. The steerable sheath catheter of claim 8 wherein the central lumen has an inner diameter and the outer jacket has an outer diameter such that the ratio of the inner diameter to the outer diameter is maximized.

* * * * *